United States Patent [19]

Lezdey et al.

[11] Patent Number: 5,190,917
[45] Date of Patent: Mar. 2, 1993

[54] TREATMENT OF PSORIASIS

[76] Inventors: John Lezdey, 976 Kingston Dr., Cherry Hill, N.J. 08034; Allan J. Wachter, 9822 S. Grandview, Tempe, Ariz. 85284

[21] Appl. No.: 683,620

[22] Filed: Apr. 11, 1991

Related U.S. Application Data

[63] Continuation-in-part of Ser. No. 598,241, Oct. 16, 1990, abandoned, and a continuation-in-part of Ser. No. 591,630, Oct. 2, 1990, Pat. No. 5,114,917, which is a continuation-in-part of Ser. No. 445,005, Dec. 4, 1989, Pat. No. 5,008,242, which is a continuation-in-part of Ser. No. 242,735, Sep. 9, 1988, abandoned, and a continuation-in-part of Ser. No. 181,707, Sep. 8, 1988, abandoned, which is a continuation-in-part of Ser. No. 946,445, Dec. 24, 1986, abandoned.

[51] Int. Cl.$^5$ .................... A61K 37/64; A61K 31/57
[52] U.S. Cl. ........................ 514/12; 514/8; 514/21
[58] Field of Search ................. 514/12, 21, 8

[56] References Cited

PUBLICATIONS

Marone et al. Clinical Immunology and Immuno-Pathology, vol. 50, pp. S24–S40 (1989).
Wasserman Am Rev. Respir. Dis. (1987) vol. 135, pp. S46–S48.
Fulcusen et al Bichem. Medicine & Metabolic Biology vol. 38, 165–169.

*Primary Examiner*—Merrell C. Cashion, Jr.
*Assistant Examiner*—Choon P. Koh
*Attorney, Agent, or Firm*—John Lezdey

[57] ABSTRACT

A method for the prophylaxis or direct treatment of dermatitis including psoriasis which comprises administering to the site of the disease an effective amount of a corticosteroid and a company which inhibits mast cells or binds with their mediators.

14 Claims, No Drawings

TREATMENT OF PSORIASIS

RELATED APPLICATION

This application is a continuation-in-part of application Ser. No. 598,241 filed Oct. 16, 1990, of Lezdey et al, now abandoned and application Ser. No. 591,630 filed Oct. 2, 1990, U.S. Pat. No. 5,114,917 which is a continuation-in-part of application Ser. No. 445,005 filed Dec. 4, 1989, U.S. Pat. No. 5,008,242 which is a continuation-in-part of application Ser. No. 242,735 filed Sep. 9, 1988, now abandoned, and application Ser. No. 181,707 filed Sep. 8, 1988, now abandoned, which are continuations-in-part of application Ser. No. 946,445 filed Dec. 24, 1986, now abandoned.

FIELD OF THE INVENTION

The present invention relates to a method and composition for treating a patient afflicted with psoriasis. More particularly, the present invention relates to the direct or prophylaxis treatment of psoriasis by topically administering synergistic amount of the combination of a compound which can inhibit mast cell proliferation or degranulation or bind with neutrophils, T-cells and their mediators, and a corticosteroid. The composition can also be used to treat chronic dermatitis, pruritis, contact dermatitis and palmoplentar eruptions.

BACKGROUND OF THE INVENTION

Psoriasis is an inflammatory skin condition whose cause is unknown. The condition involves thick scaling due to epidermal cell proliferation, cracking and bleeding. Mast cells have recently noted as being involved in psoriasis.

Inflammation is a non-specific response of tissues to diverse stimuli or insults and results in release of a variety of materials at the site of inflammation that induce pain. It is now recognized that mast cells, neutrophils and T-cells are implicated in the pathophysiology of inflammatory skin conditions as well as in other physiological disorders. Mast cells provide the greatest source of histamines in acute inflammation, as well as chymases, after degranulation by IgE.

Neutrophils are prominent in psoriatic lesions due to the potent chemoattractants released by mast cells.

Neutrophils are a main source of serine elastase and cathepsin G which are important in the tissue damage of inflammation.

The most direct approach to therapy of psoriasis skin appears to be a direct attack at the site of inflammation of the mediators of inflammation and pain and the reduction of those neutrophilic derivatives which can cause damage to the growth of new tissue during the healing process.

Disodium cromoglycate has been shown to inhibit the immediate and late-phase inflammatory reactions effectively by decreasing mast cell degranulation. Corticosteroids prevent late-phase inflammatory reactions partly by diminishing the neutrophilic infiltration triggered by mast cell degranulation. Serine protease inhibitors such as $\alpha_1$-antitrypsin and $\alpha_1$-antichymotrypsin have been found to be useful in the treatment of atopic dermatitis by inhibiting and/or binding with elastase, cathepsin G and human mast cell chymase. However, each of the prior art methods of treatment for psoriases has involved long periods of treatment without success in its long term management. It is recognized that prolong treatment with steroids can cause many side effects. Yet when a psoriasis patient is removed from steroids there is almost immediate relapse to the prior condition.

Alpha 1-antichymotrypsin is a plasma protease inhibitor synthesized in the liver. It is a single glycopeptide chain of approximately 68,000 daltons and belongs to a class of serine protease inhibitors with an apparent affinity toward chymotrypsin-like enzymes. Alpha 1-antichymotrypsin is structurally related to alpha 1-antitrypsin.

Alpha 2-macroglobulin is a glycoprotein containing 8-11% carbohydrate which can be isolated from plasma by gel filtration chromatography.

Alpha 1-proteinase inhibitor (alpha 1-antitrypsin) is a glycoprotein having a molecular weight of 53,000 determined by sedimentation equilibrium centrifugation. The glycoprotein consists of a single polypeptide chain to which several oligosaccharide units are covalently bonded. Human alpha 1-proteinase inhibitor has a role in controlling tissue destruction by endogenous serine proteinases. A genetic deficiency of alpha-1-proteinase inhibitor, which accounts for 90% of the trypsin inhibitory capacity in blood plasma, has been shown to be associated with the development of asthma and pulmonary emphysema. The degradation of elastin associated with certain inflammatory diseases probably results from a local imbalance of elastolytic enzymes and the naturally occurring tissue and plasma proteinase inhibitors. Alpha-1-proteinase inhibitor inhibits human pancreatic and leukocyte elastases. See Pannell et al, Biochemistry. 13, 5339 (1974); Johnson et al, Biochem. Biophys. Res. Commun., 72 33 (1976); Del Mar et al, Biochem. Biophys. Res. Commun., 88, 346 (1979); and Heimburger et al, Proc. Int. Res. Conf. Proteinase Inhibitors. 1st, 1-21 (1970).

The article of Groutas entitled "Inhibitors of Leukocyte Elastase and Leukocyte Cathepsin G Agents for the Treatment of Emphysema and Related Ailments" Medical Research Reviews, Vol. 7, No. 7, 227-241 (1987), discloses the role of eglin, elastinal 1 and elastin in emphysema.

Lezdey et al U.S. Pat. No. 4,916,117 discloses the treatment of pulmonary inflammation where mast cells are involved with microcrystalline alpha-1-antichymotrypsin alone or with other serine protease inhibitors.

SUMMARY OF THE INVENTION

The present invention relates to a method for treating psoriasis in patients by the topical administration of an effective amount of a corticosteroid and a compound capable of inhibiting the degranulation of mast cells and/or binding with mast cell mediators. The corticosteroid can be administered separately or in combination with the serine protease inhibiting compound. Preferably, the site is first treated with the serine protease inhibitor. Among the inhibitors of mast cell degranulation are cromylyn, serine protease inhibitors, their analogs, salts or derivatives and recombinant products. Preferable are the serine protease inhibitors which have a specific inhibiting activity of mast cells and binding with the proteases derived therefrom such as cathepsin-G, elastase, human mast cell chymase, kinins, and the like.

Among the topical corticosteroids which may be used in the present invention are triamcinolone acetonide, flurandrenolide, prednisone, amcinonide, dexamethasone, betamethasone valerate, halocinonide, clocortolone, hydrocortisone valerate, and the like.

Serine protease inhibitors have been found to play a major role in the direct inactivation of the mediators of inflammation so that the normal wound healing process can be accelerated without interference from the excess of materials released at the site of inflammation. The almost immediate disappearance of pain and itch indicates that there can be a control of the kinins as well. A cocktail of serine protease inhibitors their analogs, salts or derivatives, appears to provide the quickest healing of psoriatic lesions when used in combination with a corticosteroid.

As presently found, serine protease inhibitors are useful in the treatment of chronic psoriasis patients which not only experience pain and itch but have a problem in controlling the laydown of organized collagen because of elastase and cathepsin G; serine protease inhibitors permit healing and the growth of normal skin. The presence of the steroids enhance the healing and promote a more rapid skin growth which is initiated by the serine protease inhibitors.

It has now been found that controlling the amount of mast cells and their mediators inherently controls the amount of the destructive enzymes at the site of inflammation and prevents proliferation of the disease, prevents associated tissue damage and promotes healing. Serine protease inhibitors, for example, alpha 2-macroglobulin, alpha 1-antichymotrypsin and C-reactive protein (CRP) or cromolyn, when administered to the site of inflammation provides a reduction in swelling, pain and stiffness.

For chronic cases of dermatitis including psoriasis, a cocktail of protease inhibitors, which may include cromolyn, is preferably first administered at the site of inflammation. The treatment is then followed with the addition of a steroid.

The serine protease inhibitors which are contemplated in the present invention are any of the inhibitors, their analogs, derivatives or salts and glycosylated or monoglycosylated recombinant compounds which can inhibit mast cells or bind with any one or more of the protease derived from eosinophils, basophils and/or neutrophils such as elastase, cathepsin-G, tryptase, chymase, kinin, kallikrein, chymotrypsin, collagenase, and the like.

The serine protease inhibitors included in the present invention are alpha 1-antichymotrypsin, alpha 1-antitrypsin, alpha 2-macroglobulin, eglin, elastinal 1, elasnin 3, C-reactive protein, beta 1-antigellagenase, serine amyloid A protein, alpha cysteine protease inhibitors, inter-alpha-trypsin inhibitor, secretory leucocyte protease inhibitor, bronchial mucous inhibitor, and C-1-inhibitor. The inhibitors of the invention may be natural or prepared by recombinant means.

Eglin is particularly effective in binding with trypsin.

Alpha 1-antitrypsin has also been found especially useful in the treatment of topical inflammatory conditions because of its association with elastase and kinins. However, it is preferably used in combination with alpha 1-antichymotrypsin.

The serine protease inhibitors of the invention may be prepared by cloning, by conventional techniques utilizing an oligonucleotide probe or antibody probe, and the like. Analogs may be prepared using site specific mutagenesis. The recombinant gene product of the invention is especially useful since it is free of contaminating viruses when produced.

The analogs, salts and derivatives may be formed utilizing conventional techniques associated with other proteins without effecting the utility of the compound. There may be prepared the alkali metal salts, acid-addition salts, and esters similar to other proteins or peptides.

It is desirable to administer in some case a combination or cocktail of the serine protease inhibitors to provide a broad spectrum of drugs which can provide rapid relief of the different symptoms of psoriasis or other skin conditions. The most effective combination is alpha 1-antichymotrypsin and alpha 1-antitrypsin and/or alpha 2-macroglobulin. Preferably, the combination is administered in a ratio of 1:1:1: to 3:2:1: either in a single unit or in separate dosage form. The treatment may be simultaneous with a corticosteroid or the corticosteroid can be applied thereafter.

It is therefore an object of the invention to provide a composition which can relieve the itching and redness associated with psoriasis or dermatitis.

It is believed that the unique combination of the steroid and the serine protease inhibitor provides a two phase reaction. The steroid decreases the production of cytokines, leukotrines and interleukins which trigger mast cell secretion and a family of histamine releasing factors. The serine protease inhibitors complex with the mast cell mediators which are recognized as foreign molecules and cleared from circulation by heptocytes, macrophages and fibroblasts.

It is a yet still further object of the invention to provide a method and a composition for treating chronic skin conditions.

DETAILED DESCRIPTION OF THE PRESENT INVENTION

The objects of the present invention can be achieved by the topical administration of an affective amount of a serine protease inhibiting compound and a corticosteroid in a suitable pharmaceutical form to patients suffering from psoriasis or other skin conditions requiring steroids or other anti-inflammatory drugs.

The present invention provides a pharmaceutical composition which comprises a corticosteroid and a mast cell inhibiting compound of this invention and a pharmaceutically acceptable carrier. The mast cell inhibiting compound may be used alone or in combination with other serine protease inhibitors to provide a broad spectrum of treatment.

In accordance with one method of treatment, a 20% solution of a mast cell inhibitor such as a serine protease inhibitor, particularly $\alpha$ 1-antitrypsin, alone or in combination with other serine protease inhibitors such as $\alpha_1$-antichymotrypsin, in a sterile water or saline solution, may be sprayed on the patient at the site of the psoriatic sores or skin lesions or the area can be wrapped in soaked bandages or an occlusive dressing may be used. A corticosteroid may be included in the initial treatment. The treatment provides immediate relief of pain. The patient can then be treated with the solution daily followed by the application of a corticosteroid until the healing process is normal and the psoriasis sores or skin lesions are under control. The length of time of treatment depends upon the severity of the disease.

The pharmaceutical compositions of the present invention can be prepared utilizing conventional carriers for preparing skin creams, gels, ointments, lotions, sprays, liquids and the like. The mast cell inhibitors can be merely added to the new formulations or to topical steroidal formulations which are already prepared. The steroid and mast cell inhibitor can be formulated separately or combined in a single formulation. The amount of active ingredients is dependent upon the severity of the disease and whether or not the patient is merely on maintenance. An antioxidant may be used in the formulations to provide a longer shelf life for the mast cell inhibitor.

Initial treatment preferably begins by applying a 10-20% aqueous solution of the mast cell inhibitor to the afflicted area in chronic cases followed by a topical formulation of the steroid alone or with a mast cell inhibitor. The treatment is continued daily until the condition is under control. The amount of steroid in the formulation can be about 0.1 to 10% depending upon the condition of the patient and the steroid utilized.

Maintenance may be with a 1-10% by weight formulation of a serine protease inhibitor alone or combined with a steroid.

Among the skin disease which may be treated with the compositions of the invention are bullous skin diseases, eczema, acne, nummular dermatitis, herpes, contact dermatitis, and the like.

The following examples further illustrate the practice of this invention, but are not intended to be limiting thereof. It will be appreciated that the selection of actual amounts of mast cell inhibitors and corticosteroids to be administered to any individual patient (human or animal) will fall within the discretion of the attending physician and will be prescribed in a manner commensurate with the appropriate dosages will depend on the stage of the disease and like factors uniquely within the purview of the attending physician.

EXAMPLE I

A topical cream was prepared as follows:

| A. The following mixture was prepared: | |
|---|---|
| Triamcinolone acetonide | 2.0 g |
| $\alpha_1$-antitrypsin | 1.0 g |
| Olive oil | 5.0 g |
| Cetanol | 2.0 g |
| Stearic acid | 5.0 g |
| Glycerin aliphatic acid ester | 12.0 g |
| Tween 60 | 0.5 g |
| B. The following mixture was also prepared: | |
| Propylene glycol | 0.5 g |
| Methyl paraben | 0.1 g |
| Propyl paraben | 0.02 g |
| Purified water to | 100 g in total |

The mixture of parts A and B were blended together by conventional means to give a total of 100 g. of 100% by weight topical cream which could be utilized for treatment of mild cases of psoriasis, or other inflammatory dermatological conditions. If desired secretory leucocyte protease inhibitor and/or alpha 2-macroglobulin may be added in an amount of 2.0 g to part A.

EXAMPLE II

An oleaginous anhydrous ointment was prepared with the following composition:

| Composition | % |
|---|---|
| Dexamethasone | 2.0 |
| $\alpha_1$-antitrypsin | 5.0 |

| Composition | % |
|---|---|
| Soy phosphatide | 4.0 |
| Plastibase 50W | 85.950 |
| Butylated hydroxytoluene | 0.025 |
| Vitamin E | 0.025 |
| | 100.00 |

If desired, in lieu of alpha 1-antitrypsin as the active principal, there may utilized the combination of alpha 1-antichymotrypsin and alpha 1-antitrypsin. Other non-aqueous lipid miscible carriers may also be utilized. The composition can be used on a maintenance program to prevent the recurrence of any cell proliferation upon the first indication of inflammation.

EXAMPLE III 1000 mg of PROLASTIN, a composition sold by Cutter Biological, Miles Inc., comprising about 70% $\alpha_1$-antitrypsin and about 10-18% $\alpha_1$-antichymotrypsin was dissolved in 50 ml of saline solution. A patient suffering from psoriasis with swelling and open lesions of the hand was treated by immersing the hand in the solution. The patient was previously treated only with steroids for 3 years without success. Pain disappeared within 6-10 minutes of treatment. Treatment was continued for 1 hour. After treatment with PROLASTIN, 0.1% mometasone furoate was applied. The treatment was continued with alternate day application of PROLASTIN and daily applications of mometasone furoate.

After three weeks all of the symptoms of psoriasis disappeared and 90% of the skin rash disappeared.

The same procedure is effective in treating the symptoms of psoriatic arthritis.

Example IV

A suitable cream for topical use was prepared by admixing 43 g of PROLASTIN from Cutter Biological Laboratories, with 6 ml of water and 1000 g of a balm available under the trademark AQUAPHOR, sold by Beiesdorf Inc., Norwalk, Conn. AQUAPHOR comprises a mixture of petrolatum, mineral oil, wax and, wool wax alcohol.

The cream is useful for the prophylaxis treatment of psoriasis.

We claim:

1. A method for the treatment of dermatitis or psoriasis which comprises topically administering to the site of the psoriasis or dermatitis an effective amount of the combination of at least one compound having an affinity to bind and/or inhibit the mediators of mast cells and T-cells and of about 0.1 to 10% by weight of a corticosteroid.

2. The method of claim 1 wherein said inhibitor of mast cell mediators is a serine proteases inhibitor, its salts, derivatives or analogs.

3. The method of claim 2 wherein said serine protease inhibitor is selected from the group consisting of alpha 1-antitrypsin, alpha 1-antichymotrypsin, secretory leucocyte protease inhibitor, C-reactive protein, serum amyloid A protein, alpha 2-macroglobulin, eglin, elasnin 3 and elastinal.

4. The method of claim 2 wherein said serine protease inhibitor is recombinant.

5. The method of claim 1 wherein said inhibitor of the mediators of mast cells is cromolyn.

6. The method of claim 1 wherein said corticosteroid is selected from the group consisting of triamcinolone acetonide, prednisone, hydrocortisone valerate, dexamethasone flurandrenolide and mometasone furoate.

7. The method of claim 1 wherein said corticosteroid and said inhibitor of mast cell mediators are administered simultaneously.

8. The method of claim 1 wherein said corticosteroid and said inhibitor of mast cell mediators are administered separately.

9. A pharmaceutical composition for the topical treatment of dermatitis or psoriasis comprising the combination of about 0.1 to 10% by weight of a corticosteroid and a compound capable of inhibiting and/or binding with the mediators of mast cells and T-cells.

10. The pharmaceutical composition of claim 9 wherein said inhibitor of mast cell mediators is a serine protease inhibitor.

11. The pharmaceutical composition of claim 10 wherein said serine protease inhibitor is selected from the group consisting of $\alpha_1$-antitrypsin and $\alpha_1$-antichymotrypsin.

12. The pharmaceutical composition of claim 9 wherein said inhibitor of mast cell mediators is cromolyn or a salt or derivative thereof.

13. The pharmaceutical composition of claim 9 wherein said corticosteroid is selected from the group consisting of triamcinolone acetonide, prednisone, hydrocortisone valerate, dexamethasone, flurandrenolide and mometasone furoate.

14. The pharmaceutical composition of claim 9 comprising triamcinolone acetonide and cromolyn.

* * * * *